United States Patent [19]

Lidor et al.

[11] Patent Number: 5,069,905
[45] Date of Patent: Dec. 3, 1991

[54] METHOD AND COMPOSITIONS COMPRISING A VITAMIN D DERIVATIVES FOR THE LOCAL TREATMENT OF BONE FRACTURES

[75] Inventors: Cobi Lidor, Herzeliya; Samuel Dekel, Ramat-Gan; Samuel Edelstein, Rehovot; Michael S. Meyer, Tel-Aviv, all of Israel

[73] Assignee: Yeda Research and Development Company Limited, Israel

[21] Appl. No.: 385,816

[22] Filed: Jul. 26, 1989

Related U.S. Application Data

[63] Continuation of Ser. No. 840,511, Mar. 17, 1986, abandoned.

[30] Foreign Application Priority Data

Mar. 15, 1985 [IL] Israel ........................................ 74617

[51] Int. Cl.$^5$ .......................... A61F 2/00; A61K 31/59
[52] U.S. Cl. .................................... 424/423; 424/422; 514/167; 514/171; 623/16
[58] Field of Search ........................... 514/167, 171, 2; 424/422, 423; 623/16

[56] References Cited

U.S. PATENT DOCUMENTS

| | | | |
|---|---|---|---|
| 4,364,941 | 12/1982 | Kiyoki et al. | 424/236 |
| 4,590,184 | 5/1986 | Maeda et al. | 514/167 |
| 4,671,263 | 6/1987 | Draenert | 128/92 |
| 4,778,471 | 10/1988 | Bajpai | 623/16 |
| 4,822,609 | 4/1989 | Flora | 514/167 |
| 4,851,401 | 7/1989 | DeLuca et al. | 514/167 |
| 4,911,641 | 3/1990 | Detsch | 433/228.1 |
| 4,929,610 | 5/1990 | Meier et al. | 514/167 |
| 4,973,168 | 11/1990 | Chan | 366/139 |

FOREIGN PATENT DOCUMENTS

| | | |
|---|---|---|
| 198213 | 10/1986 | European Pat. Off. |
| 276573 | 8/1988 | European Pat. Off. |
| 295827 | 12/1988 | European Pat. Off. |
| 301167 | 2/1989 | European Pat. Off. |

OTHER PUBLICATIONS

Lidor et al. GA. 107:161674R(1987) Of EP. 198213 22 Oct. 1986.
Lidor et al. GA. 106:194034Q(1987).
Lidor et al. GA. 106:83397R(1987).
Lidor et al. GA. 104:87440F(1986).
Arkhapchev et al. GA. 101:209607B(1984).
Arkhapchev et al. GA. 100:137805U(1984).
Dekel et al. GA. 99:1385312(1983).
Blazheevich et al. GA. 98:33562M(1983).
Lindgren et al. GA. 95:215523V (1981) "Effects of 1,25 Dihydroxy Vit $D_3$ and Calcitonin on Fracture Healing in Adult Rats".
Bordier, P. A., et al., J. Clin. Endocrinol. Metab. vol. 46, No. 2, p. 284 (1978).
Kanis, J. A., et al., Br. Med. J. 1, p. 1382 (1978).
Karis, J. A., et al. British Medical Journal (24 Mar. 1979), p. 822.
Ornoy, A, et al., Nature, vol. 276, p. 517 (1978).
Endo, J. H., et al., Nature, vol. 286, p. 262 (1980).

(List continued on next page.)

Primary Examiner—Shep K. Rose
Attorney, Agent, or Firm—Steinberg & Raskin

[57] ABSTRACT

A method for the treatment and promotion of healing of bone fractures and osteotomies in warm-blooded animals including humans, which comprises local application to the site of the fracture or osteotomy of a therapeutically effective amount of $24,25(OH)_2D_3$ dissolved or dispersed in a suitable physiologically compatible carrier.

There are also provided, for use in the above method, compositions comprising from 0.002 to 0.2% by weight of $24,25(OH)_2D_3$ in combination with a physiologically compatible vehicle suitable for use in orthopedic surgery for local application to a site of bone fracture or osteotomy, or for application to solid or semi-solid implants conventional in orthopedic surgery and to prostheses.

19 Claims, 11 Drawing Sheets

OTHER PUBLICATIONS

Brumbaugh, P. F., et al. Am. J. Pathology vol. 106, No. 2, pp. 171–179 (1982).
Dekel, S., et al., Clin. Sci. 65, p. 429 (1983).
Blazheevich, N.V., et al. Vopr. Med. Khim. vol. 28, No. 6, 98–105 (1982).
Corvol, M. T., et al., Endocrinology vol. 102, No. 4, p. 1269 (1978).
Tam. C. S., et al. Endocrinology vol. 118, No. 6, p. 2217 (1986).
Haussler, M. R., et al. No. Eng. J. Med. 297, p. 974 (Nov. 3, 1977).
Salomon, C. D., Calc. Tiss. Res. 15, 201–212 (1979).
Kahn, S. E., et al., Calc Tiss. Res. 25, 85–92 (1978).
Engstrom, C., et al., Acta Orthop Scand. 53, 317–323 (1982).
Shedden, R., et al., Calc. Tiss. Res. 22, 19–25 (1976).
Noff, D., et al. Journal of Molecules Medicine, 3, 147–155 (1978).

METHOD AND COMPOSITIONS COMPRISING A VITAMIN D DERIVATIVES FOR THE LOCAL TREATMENT OF BONE FRACTURES

This is a continuation, of application Ser. No. 840,511, filed Mar. 17, 1986, now abandoned.

BACKGROUND OF THE INVENTION

The present invention relates to a novel method for the treatment and promotion of healing of bone fractures and osteotomies in warm-blooded animals including humans, by the local application of 24,25-dihydroxycholecalciferol (24,25-dihydroxy vitamin $D_3$, hereinafter "24,25$(OH)_2D_3$"). The invention further relates to novel compositions comprising 24,25$(OH)_2D_3$ adapted for the local application to the sites of bone fractures or osteotomies in accordance with the method of the invention.

Vitamin $D_3$, cholecalciferol, has been long known to be associated with bone formation. Several publications provided evidence that 24,25-dihydroxycholecalciferol (24,25$(OH)_2D_3$) is the active metabolite in this process. (Bordier, P. A. et al., J. Clin. Endocrinol. Metab. 46, 284 (1978); Kanis, J. A. et al., Br. Med. J. 1, 1382 (1978); Ornoy, A. et al., Nature 276, 517 (1978); and Endo, J. H. et al., Nature 286, 262 (1980). More recently Brumbaugh et al., Am. J. Pathology 106, 171 (1982); Dekel, S. et al., Clin. Sci. 65, 429 (1983); and Blazheevich, N. V. et al., Vopr. Med. Chim. 28 (6), 98–105 (1982) showed that systemic administration of 24,25$(OH)_2D_3$ promotes bone repair and union in experimental fractures. In all these studies, 24,25$(OH)_2D_3$ was administered to the animals or human patients by intravenous or subcutaneous injection into the muscle or by the oral route, and there was no indication nor any hint in the prior art that local administration to the fracture site of this vitamin $D_3$ metabolite might have any effect on fracture healing.

SUMMARY OF THE INVENTION

It has now been surprisingly found in accordance with the present invention that local administration of 24,25$(OH)_2D_3$ to the site of bone fractures or osteotomies in warm-blooded animals including humans, unexpectedly results in an excellent healing effect of said fractures or osteotomies, the effect being considerably superior to those obtained by hitherto conventional treatments. It has further been found that this beneficial effect on fracture healing is practically unique to 24,25$(OH)_2D_3$ and is not, or only insignificantly, exhibited by other vitamin $D_3$ metabolites, in particular $1\alpha$,25-dihydroxy vitamin $D_3$ (hereinafter "1,25$(OH)_2D_3$").

The invention thus provides, in accordance with one aspect thereof, a method for the treatment and promotion of healing of bone fractures and osteotomies in warmblooded animals including humans, which comprises local application to the site of the fracture or osteotomy of a therapeutically effective amount of 24,25$(OH)_2D_3$ dissolved or dispersed in a suitable physiologically compatible carrier.

Local administration of 24,25$(OH)_2D_3$ to the sites of bone fractures or osteotomies, can be effected either by injection of the active metabolite in a suitable solvent (preferably an oily solvent, e.g. arachis oil) to the cartilage growth plate or, in cases of open surgery, by local application thereto of the active vitamin $D_3$ metabolite dissolved or dispersed in a suitable solvent or any other vehicle or carrier selected from those suitable for use in orthopedic surgery, such as bone-wax, demineralized bone powder, polymeric bone cements, bone sealants and the like. Alternatively, local application can be achieved by applying a solution or dispersion of the active metabolite in a suitable vehicle onto the surface of, or incorporating it into solid or semi-solid implants conventionally used in orthopedic surgery, such as dacron-mesh, gel-foam and kiel bone, or prostheses.

In accordance with a further aspect, the invention provides compositions adapted for use in the method of the invention, comprising from 0.002 to 0.2% by weight of 24,25$(OH)_2D_3$ in combination with a physiologically compatible vehicle (as hereinafter defined) suitable for use in orthopedic surgery for local application to a site of bone fracture or osteotomy, or for application to solid or semi-solid implants conventional in orthopedic surgery and to prostheses.

Preferably the compositions according to this aspect of the invention comprise from 0.005 to 0.05% by weight of 24,25$(OH)_2D_3$.

The terms "vehicle" or "carrier" as used herein are meant to refer to any liquid, semi-solid or solid materials, either synthetic or of animal origin, which are conventionally used in orthopedic surgery.

Suitable vehicles or carriers for use in the compositions according to the invention include bone-wax, demineralized bone powder, polymeric bone cements and various conventional bone sealants, e.g. "Absele" (Trade Mark). As stated above, 24,25$(OH)_2D_3$ can also be applied, according to the invention, to the surface of prostheses or solid or semi-solid orthopedic implants or incorporated therein, e.g. by absorption in such implants which have a porous structure, e.g. dacron mesh, the so-called gel-foam, kiel bone and the like.

In accordance with the present invention it has first been found that local administration of 24,25$(OH)_2D_3$ in vivo by injecting into the proximal cartilage growth plate of the tibiae of vitamin D-deficient chicks, resulted in disappearance of the rachitic lesions. Similar administration of 1,25$(OH)_2D_3$ failed to show any sign of healing. These findings are consistent with previously published data suggesting that 24,25$(OH)_2D_3$ is the most potent metabolite for healing rickets and probably plays a direct role in endochondral bone formation and that, furthermore, it is probably important for differentiation and maturation of the growth plate cartilage which has to be replaced by bone.

In the light of the above findings, another set of experiments was designed in order to demonstrate the effect of locally administered 24,25$(OH)_2D_3$ in facilitating fracture healing. Experimental fractures were made in the mid-shaft of the tibiae of vitamin D-deficient chicks and a composition comprising 0.1% by weight of 24,25$(OH)_2D_3$ in bone-wax was implanted at the fracture site. A control group of chicks were treated in the same manner except that at the fracture site there was implanted bone-wax without the active vitamin $D_3$ metabolite. A number of birds of both groups were killed 9 and 12 days after the fracture, calcium level in the plasma was determined and the calluses formed at the fractured tibiae were examined histologically. Both groups of chicks were found to be hypocalcaemic, indicating that the vitamin $D_3$ metabolite implanted at the fracture site did not enter the blood stream. It could be observed already macroscopically that the calluses formed after 9 and 12 days in the 24,25$(OH)_2D_3$-treated chicks were considerably larger as compared to the control group, and after 12 days the two edges of the bones at the site of the fracture in the treated group were significantly less mobile than in the control fractures.

Histological examination of the calluses revealed three major differences between the control and the treated chicks:

(a) The cells in the calluses formed at the fracture sites of the control group were still undifferentiated cartilage cells of proliferative nature. In calluses formed in the $24,25(OH)_2D_3$-treated chicks, the majority of cells were well differentiated and hypertrophic.

(b) Relatively larger numbers of blood vessels were found in the calluses formed in the $24,25(OH)_2D_3$-treated group as compared with the control group calluses, and the appearance of mesenchymal cells (osteoblasts) and formation of osteoid were noted around vessels in the $24,25(OH)_2D_3$-treated calluses, while none were observed in the control group.

(c) In the $24,25(OH)_2D_3$-treated group, but not in the control group, there was observed formation of new trabeculae with mineralization.

A similar set of experiments was carried out on normal, vitamin D-supplemented chicks. The experimental protocol was identical to the one used with the vitamin D-deficient birds and similar results were observed.

The process of fracture-healing which is in principle a process of endochondral bone formation, involves the participation of various types of cells. The initial process in bone formation is the proliferation of the cartilage cells (chondroblasts). A distinct solid, extracellular matrix is being formed and the cells become hypertrophic. Mineralization appears in the extracellular matrix and thereafter the mineralized cartilage is resorbed by chondroclasts and mesenchymal and osteoblast cells appear and deposit new bone.

$24,25(OH)_2D_3$ was shown to affect the maturation, differentiation and function of cartilage cells (Corvol, M. T. et al., Endocrinology 102, 1269 (1978); Endo, J. H. et al., Nature 286, 262 (1980); Ornoy, A. et al., Nature 276, 517 (1978)). In the absence of this metabolite the maturation of cartilage cells is blocked, resulting in lack of endochondral ossification. One of the most important steps in the process of fracture healing is the formation of a cartilaginous callus in which proliferative cells are maturing to hypertrophic cells which are then replaced by bone, similar to the mechanism in the epiphyseal growth-plate. $24,25(OH)_2D_3$ locally applied to the site of the callus formation is most likely taken up by the cells at a very early stage in the process of callus formation, and the entire process is facilitated, as was indeed shown by the above experiments. Faster formation of the callus with faster maturation of the cells will, therefore, result in a faster healing of the fracture and repair of osteotomy.

$24,25(OH)_2D_3$ was shown in accordance with the present invention to affect the maturation and differentiation of cartilage cells, namely, the initial stages in the process of bone formation. However, several other factors that are known to affect cells participating in the later stages of said process could be advantageously used in order to further shorten the time required for fracture healing. Thus, local application of $1\alpha(OH)D_3$ and/or $1,25(OH)_2D_3$ in combination with $24,25(OH)_2D_3$ at the fracture site could result, not only in faster maturation of cartilage cells, but also in more rapid formation of bone due to an additional effect of $1,25(OH)_2D_3$ on osteoblast activity of these cells. Additional substances which may facilitate fracture healing if applied locally together with $24,25(OH)_2D_3$ at the fracture site include estradiol, hydroxyapatite crystals, fluoroapatite crystals and growth-hormone. All these factors are known to stimulate and facilitate fracture healing and bone formation.

Thus, the invention also contemplates within its scope a method for the treatment and promotion of healing of bone fractures and osteotomies in warm-blooded animals including humans, which comprises local application to the site of the fracture or osteotomy of $24,25(OH)_2D_3$ in a suitable carrier in combination with one or more auxiliary substances selected from $1\alpha(OH)D_3$, $1,25(OH)_2D_3$, estradiol, hydroxyapatite crystals, fluoroapatite crystals and growth-hormone.

In its other aspect, the invention extends to compositions comprising from 0.002 to 0.2% by weight of $24,25(OH)_2D_3$ in combination with a therapeutically effective amount of one or more of the above-listed auxiliary substances.

BRIEF DESCRIPTION OF THE DRAWINGS

The invention will now be illustrated by the following non-limiting examples and with reference to the accompanying drawings in which.

DESCRIPTION OF THE PREFERRED EMBODIMENTS

Example 1

2.5 g of bone-wax were heated on a water bath to 55° C. and to the melt there was added a solution of 250 $\mu$g of $24,25(OH)_2D_3$ in 0.5 ml of ethanol. The mixture was stirred at about 55° C. for several seconds and immediately cooled in an ice bath.

A sample of the mixture obtained above was extracted with chloroform-methanol, the extract was evaporated to dryness and the lipid residue submitted to HPLC analysis. The resulting graph was compared with that obtained from the chloroform-methanol extract of the same bone-wax which did not contain the vitamin $D_3$ metabolite. The only difference between the curves was an additional peak which appeared in the curve obtained from the first-mentioned sample which peak was identified as the $24,25(OH)_2D_3$ peak. This proved that the vitamin $D_3$ metabolite did not undergo any chemical change in the course of the above-described procedure.

Example 2

2 mg of 24,25(OH)$_2$D$_3$ were dissolved in 10 ml of the liquid monomeric component of bone cement. In use, the desired amount of the obtained solution is admixed with prescribed amount of the polymeric component (powder) of the cement, the mixture applied to the fracture site and allowed to set.

Example 3

A solution of 200 μg of 24,25(OH)$_2$D$_3$ in 1 ml of ethanol was intimately admixed with 2 g of a conventional absorbable bone sealant (main components: ox fibrin, ox collagen, dextran, glycerol, water) by kneading in a glass mortar at room temperature.

Example 4

500 μg of 24,25(OH)$_2$D$_3$ were dissolved in 3 ml of ethanol and the solution intimately admixed with collagen bone powder. The ethanol solvent was then evaporated under reduced pressure at room temperature.

Example 5

Healing of rachitic lesions in chicks by local administration of 24,25(OH)$_2$D$_3$ into the bone One day old male chicks (Gallus domesticus) were depleted of vitamin D by feeding them a vitamin D-deficient diet for 4 weeks. They were then divided into four groups and injected directly into the proximal epiphysis of the tibia, every 3 days, with one of the following:
(a) 10 μl of arachis oil;
(b) 10 μl of arachis oil containing 3 μg of 24,25(OH)$_2$D$_3$;
(c) 10 μl of arachis oil containing 1 μg of 1,25(OH)$_2$D$_3$; and
(d) 10 μl of arachis oil containing 5 μg of 25-hydroxycholecalciferol (25(OH)D$_3$).

The oily solutions containing the vitamin D$_3$ metabolites were injected into the right tibia and the vehicle (arachis oil) only—into the left tibia.

Two additional groups of chicks were studied and served as non-treated controls: a group of rachitic birds and a group of vitamin D$_3$-supplemented birds.

Following a course of three intraephiphyseal injections the chicks were killed and plasma was prepared for the determination of calcium and of vitamin D$_3$ metabolites. The proximal epiphyses of the tibiae were removed, fixed in 10% neutral formaldehyde, then dehydrated, and embedded in glycol methacrylate. Non-decalcified, 3 μm thick longitudinal sections were stained with toluidine blue or von Kossa stain and examined by light microscopy. The results are summarized in the following Table I.

TABLE I

Plasma concentration of calcium and the hydroxylated metabolites of cholecalciferol compared with histological assesment of bone.

| Treated group | | plasma Ca (mg %) | 25(OH)D$_3$ (ng/ml) | 24,25(OH)$_2$D$_3$ (ng/ml) | 1,25(OH)$_2$D$_3$ (pg/ml) | No. of histol. specimens examined | Length of proximal tibial epiphysis (mm) | Width of osteoid seams in metaphysis. (μm) | No. of osteoclasts/ mm$^2$ in metaphysis |
|---|---|---|---|---|---|---|---|---|---|
| +D | | 11.2 ± 0.2*$^a$ | 22.5 ± 2.5*$^a$ | 3.6 ± 0.6*$^a$ | 34.5 ± 7.6*$^b$ | 6 | 3.5 ± 0.52$^a$ | 3.6 ± 1.13$^a$ | 19.0 ± 1.6$^a$ |
| −D | | 6.7 ± 0.6$^b$ | ND** | ND | ND | 13 | 7.6 ± 0.24$^b$ | 10.2 ± 1.76$^b$ | 24.0 ± 1.6$^b$ |
| | Vehicle - R*** | | | | | | | | |
| −D | | | | | | 14 | | | |
| | Vehicle - L | 7.1 ± 0.5$^b$ | — | — | — | | 7.0 ± 0.14$^b$ | 12.5 ± 0.92$^b$ | 27.0 ± 1.5$^b$ |
| | 24,25(OH)$_2$D$_3$ - R | | | | | 10 | 4.8 ± 0.16$^a$ | 4.5 ± 0.23$^a$ | 24.0 ± 1.3$^b$ |
| −D | | 8.3 ± 0.6$^b$ | ND | ND | ND | | | | |
| | Vehicle - L | | | | | 7 | 6.1 ± 0.22$^b$ | 8.2 ± 0.47$^b$ | 23.0 ± 1.9$^b$ |
| | 1,25(OH)$_2$D$_3$ - R | | | | | 4 | 6.8 ± 0.50$^b$ | 12.5 ± 0.86$^b$ | 37.0 ± 2.6$^c$ |
| −D | | 6.8 ± 0.3$^b$ | ND | ND | ND | | | | |
| | Vehicle - L | | | | | 4 | 6.4 ± 0.36$^b$ | 11.1 ± 0.55$^b$ | 34.0 ± 3.2$^c$ |
| | 25(OH)D$_3$ - R | | | | | 6 | 4.6 ± 0.50$^a$ | 4.2 ± 0.41$^a$ | 29.0 ± 1.2$^b$ |
| −D | | 10.6 ± 0.1$^a$ | 7.9 ± 1.2$^b$ | 1.4 ± 0.1$^b$ | 14.8 ± 0.3$^b$ | | | | |
| | Vehicle - L | | | | | 4 | 5.6 ± 0.38$^b$ | 6.3 ± 0.86$^a$ | 35.0 ± 1.1$^c$ |

*MEAN of 6 chicks ± SEM
**ND: non-detectable
***R and L: right and left tibia, respectively.
Means bearing a common superscript within a column are not significantly different (P > 0.05).

As shown in Table I, the vitamin D-deficient chicks that were injected intraepiphyseally with 1,25(OH)$_2$D$_3$ or with 24,25(OH)$_2$D$_3$ retained low plasma concentrations of calcium, similar to untreated vitamin D-deficient birds. None of the hydroxylated vitamine D$_3$ metabolites could be detected in the plasma of these chicks, indicating that the injected metabolite did not enter the blood stream. However, the chicks that were injected intraepiphyseally with 25(OH)D$_3$ showed normal plasma concentration of calcium and detectable levels of the hydroxylated metabolites, although significantly lower than the levels measured in the vitamin D-supplemented group.

The upper tibial epiphyses in all birds were still cartilaginous consisting of reserve, proliferative and hypertrophic zones. In the controls (+D) the different zones were well defined. Vitamin D-deficient chicks revealed typical signs of rickets, i.e. elongated proliferative and hypertrophic zones, wide osteoid seams with little mineralization of cartilage. However, it was difficult to clearly differentiate between the proliferative and hypertrophic zones and the measurements are related to total epiphyseal length only rather than to individual zones (see Table I).

The results prove that injection of 1,25(OH)$_2$D$_3$ did not reduce the severity of the rickets, whereas injection of 24,25(OH)$_2$D$_3$ caused almost complete recovery of the right tibia, while the left tibia still showed typical rachitic changes except for a slight reduction in total epiphyseal length. Injection of 25(OH)D$_3$ was followed by recovery from rickets in both right and left tibiae although the recovery was more pronounced in the right tibia, the injected one. Furthermore, treatment with all metabolites resulted in a significant increase in the number of osteoclasts as compared to +D chicks. This was most prominent following 1,25(OH)$_2$D$_3$ treatment.

Example 6

Promotion of bone formation by local application of 24,25(OH)$_2$D$_3$ in bone-wax to the site of the fracture One-day old male chicks (Gallus domesticus) were depleted of vitamin D by feeding them a vitamin D-deficient diet for four weeks. Experimental fractures were performed under general anasthesia with continuous inhalation of Halotane. A skin incision was made under sterile conditions, the tibia was exposed and a transversal hole was drilled with the aid of a dental burr. Light pressure with the fingers caused transversal fracture of the bone. About 50 mg of bone-wax containing 5 $\mu$g of 24,25(OH)$_2$D$_3$, prepared as described in Example 1 herein, was implanted at the fracture site on both edges of the fractured tibia. After 9 and 12 days some of the chicks were killed, plasma was prepared for calcium determination and the calluses of the fractured tibiae were removed, fixed in 10% neutral formaldehyde and prepared routinely for light microscopy. Decalcified preparations were made for Hematoxilyn and Eosin (H&E) staining and undecalcified preparations were made for von Kossa stain. A control group of chicks were treated in the same manner except that 50 mg of bone-wax which did not contain any 24,25(OH)$_2$D$_3$ was implanted at the fracture site.

Both groups of chicks were hypocalcemic, indicating that the vitamin D$_3$ metabolite implanted at the fracture site did not enter the blood stream. The calluses formed after 9 and 12 days revealed macroscopically the formation of a larger callus at the fracture sites where 24,25(OH)$_2$D$_3$ in bone-wax was implanted as compared to the control group. On the 12th day after the fracture it was further observed in the treated group that the two edges of the bones at the fracture site were significantly less mobile than in the control group.

Figure 1:
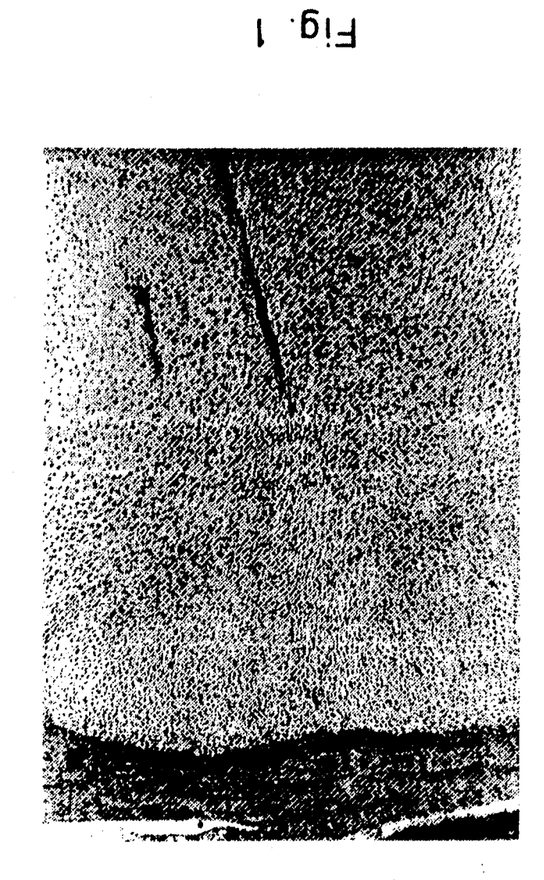
FIGS. 1, 2 and 3 are light microscopical views of 3 $\mu$m thick longitudinal sections from the callus of the tibiae of vitamin D-deficient chicks of the control group in Example 6 herein, taken 9 days after the experimental fracture.
Figure 2:
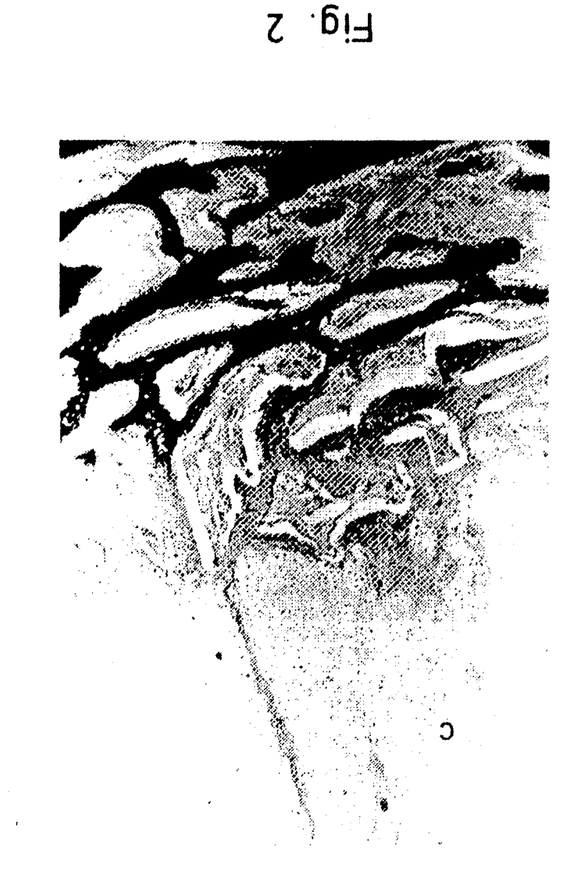
Figure 3:
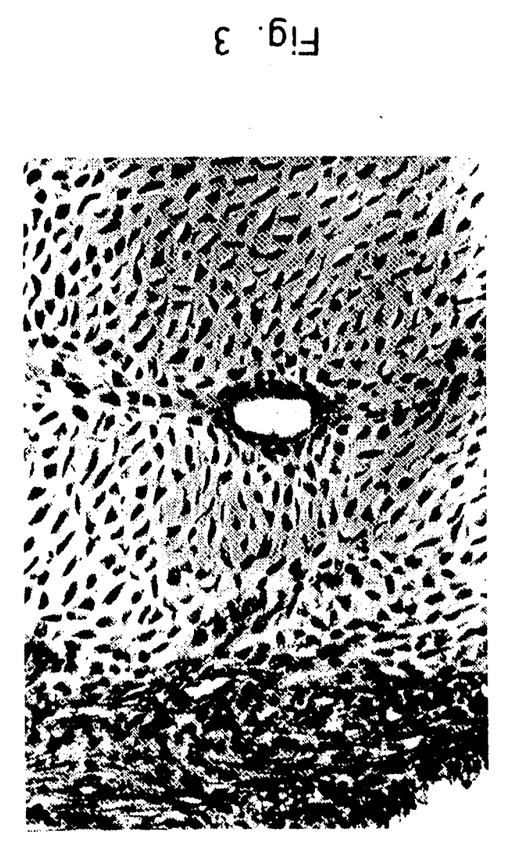

The histological findings are illustrated in FIGS. 1 to 18 of the accompanying drawings in which the following can be seen:

FIGS. 1, 2 and 3 are microscopical views at magnifications of $\times$70 (FIGS. 1 and 2) and $\times$280 (FIG. 3) of preparations taken from chicks of the D-deficient control group, 9 days after the fracture. In FIGS. 1 and 3 (H&E stain) the appearance of the cartilage cells is the same, with very few blood vessels and no osteoblasts surrounding them. In FIG. 2 (von Kossa stain) there is no calcification in the cartilage area (C).

Figure 4:
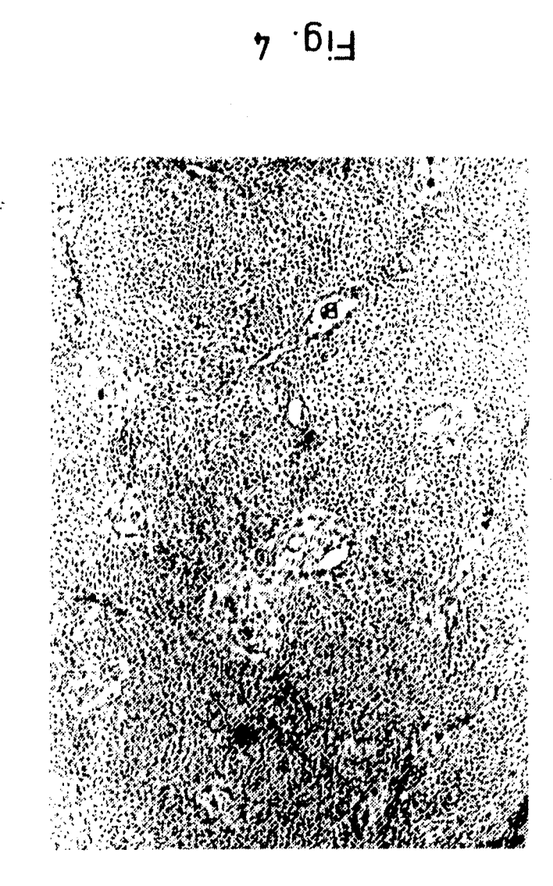
FIGS. 4 to 7 are similar views to those in FIGS. 1 to 3 of preparations taken from the $24,25(OH)_2D_3$-treated group of chicks in Example 6, 9 days after the experimental fracture.
Figure 5:
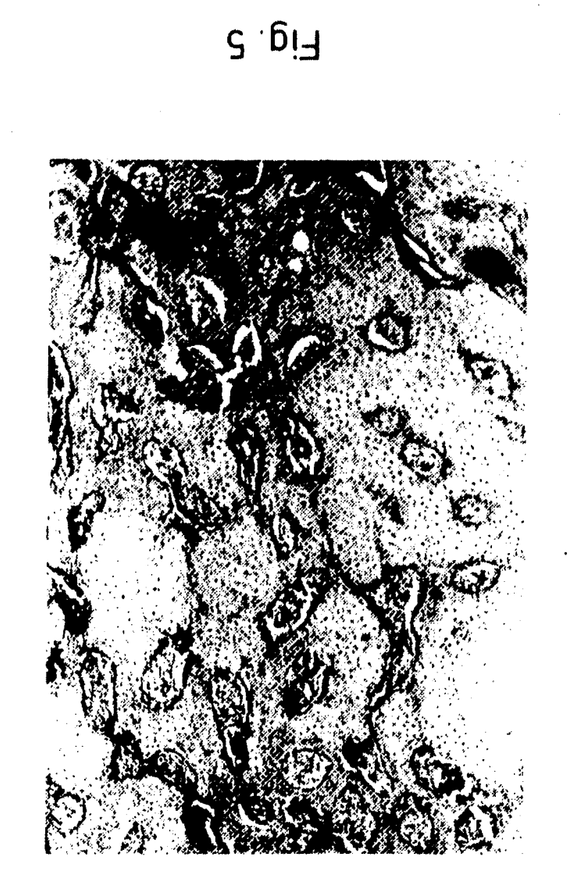
Figure 6:
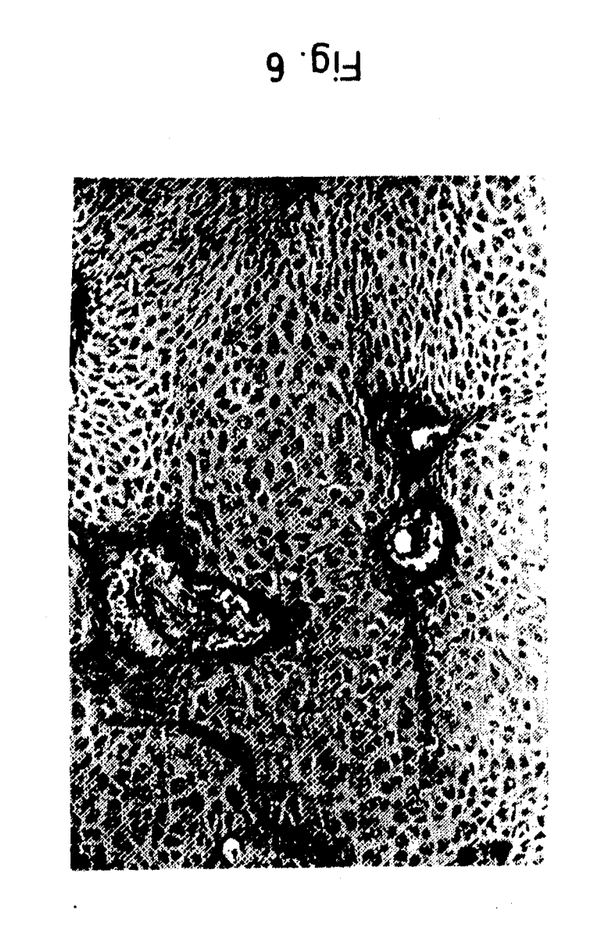
Figure 7:
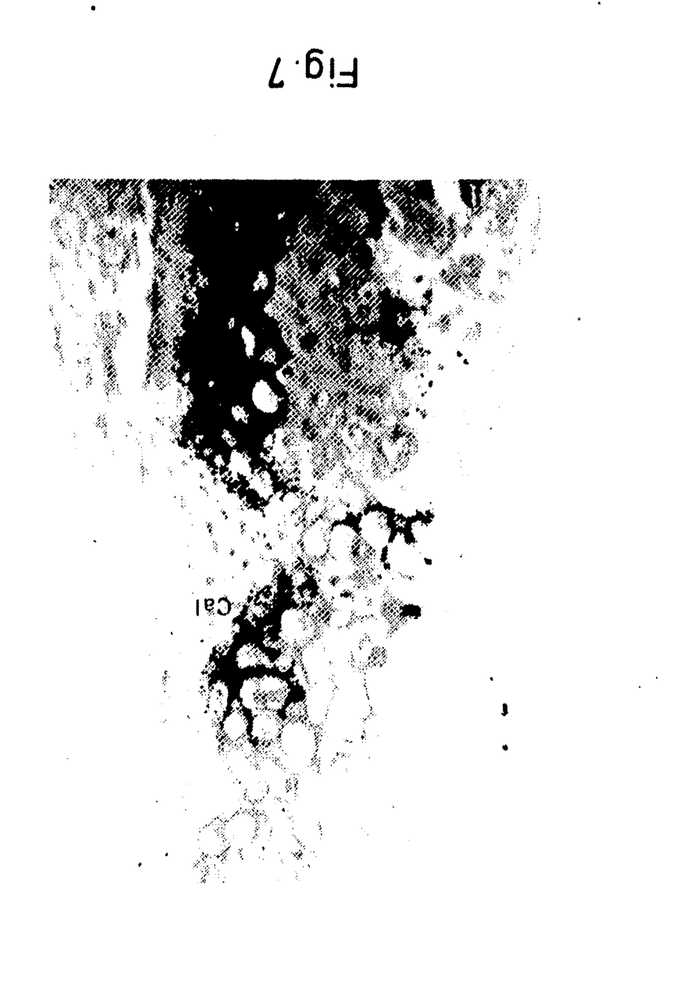

In FIGS. 4 and 5 (magnification $\times$70) and 6 and 7 (magnification $\times$280) which were taken from the 24,25(OH)$_2$D$_3$-treated chicks 9 days after the fracture, there can be seen a large number of blood vessels (B in FIGS. 4 and 5) within the cartilage milieu with the beginning of osteoid formation (+) and calcification ("Cal" in FIG. 7, von Kossa stain). The chondrocytes are of different sizes and shapes (FIG. 6).

Figure 8:
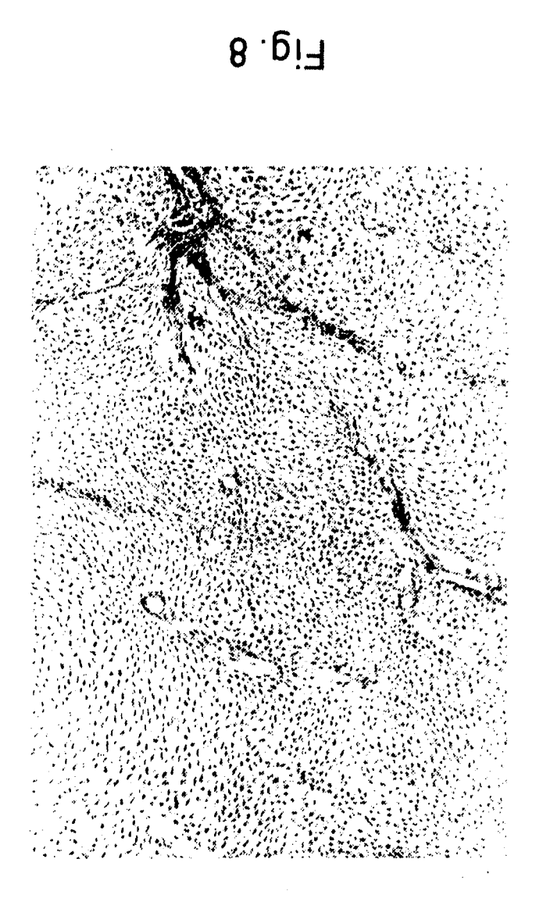
FIGS. 8 to 10 are similar views to those of FIGS. 1 to 3 of preparations taken from vitamin D-deficient chicks of the control group in Example 6, 12 days after the experimental fracture.
Figure 9:
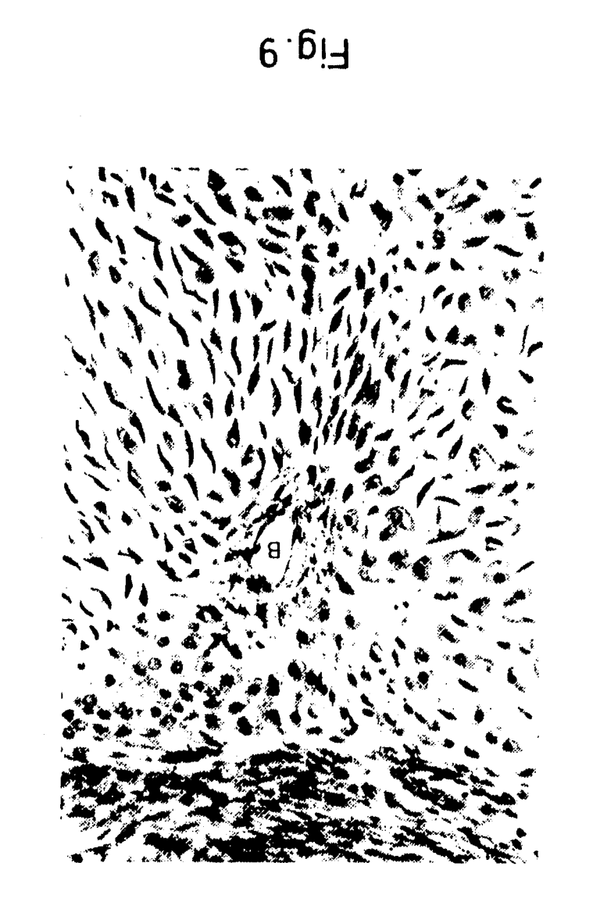
Figure 10:
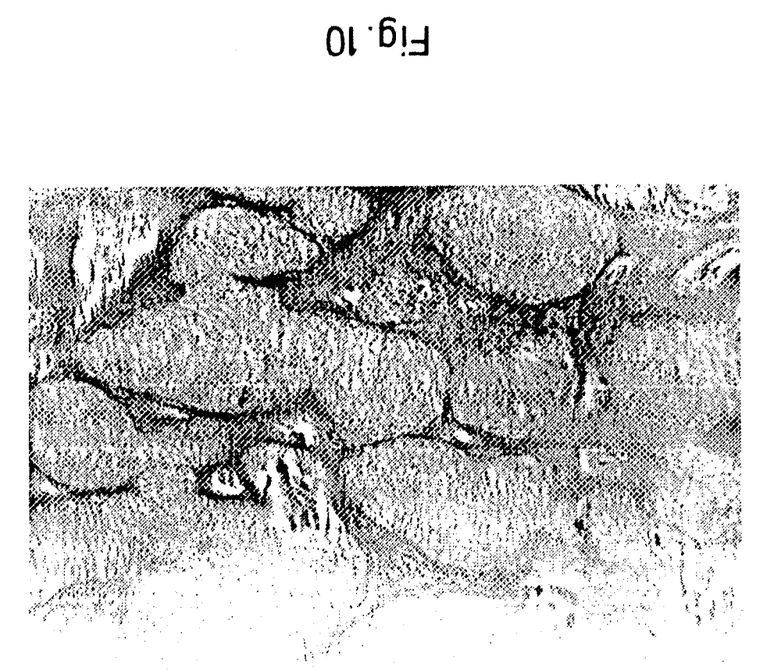
Figure 11:
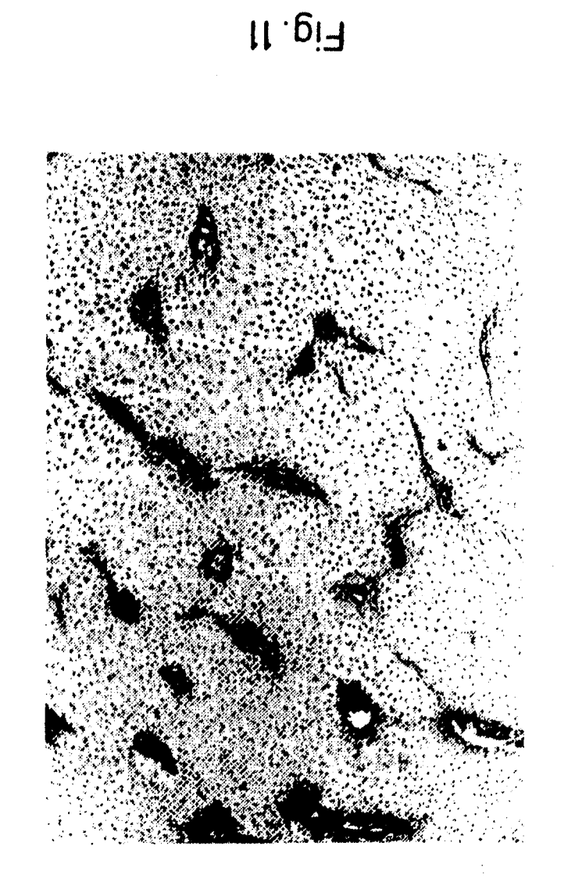
FIGS. 11 to 18 are similar views to those of FIGS. 1 to 3 of preparations taken from the $24,25(OH)_2D_3$ treated chicks in Example 6, 12 days after the experimental fracture.
Figure 12:
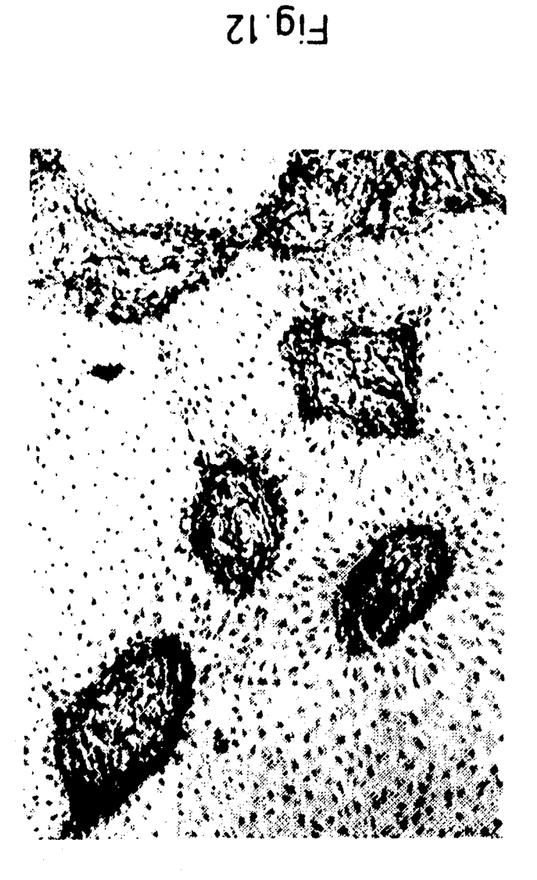

In FIGS. 8 to 10 which were taken from the D-deficient control group chicks 12 days after the fracture, there are still very few blood vessels (B in FIG. 9, magnification $\times$280) with no differentiation in the cartilaginous tissue and no calcifications (FIG. 10, von Kossa stain, magnification $\times$70).

Figure 13:
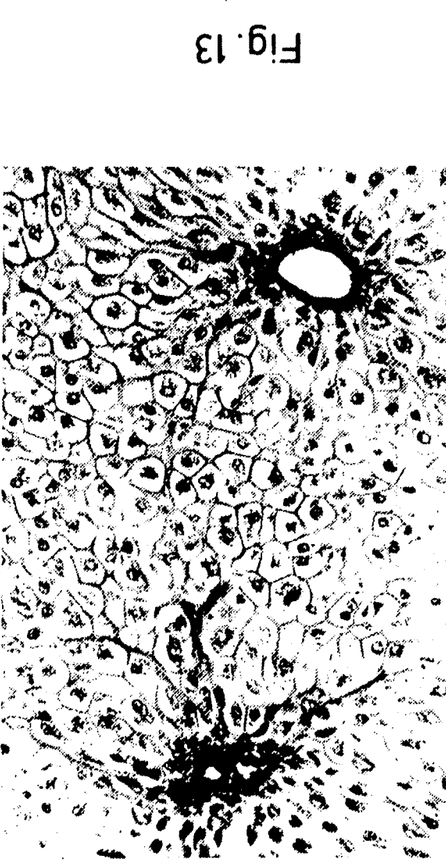
Figure 14:
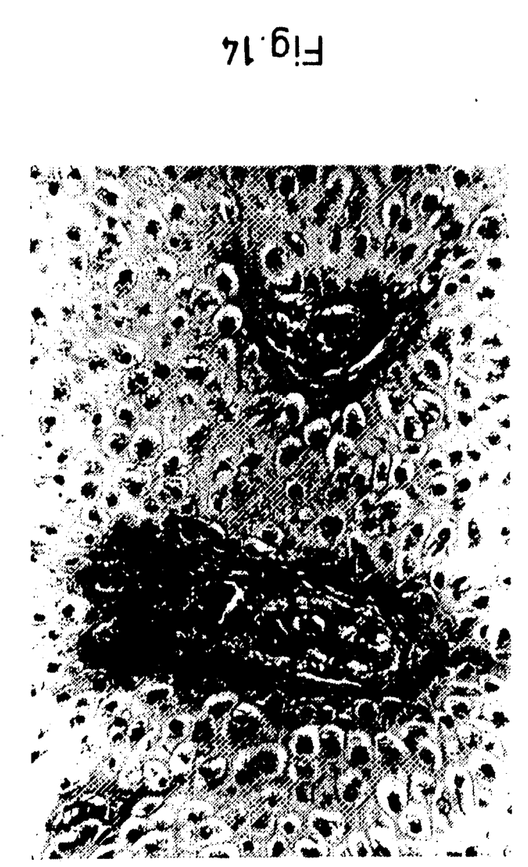
Figure 15:
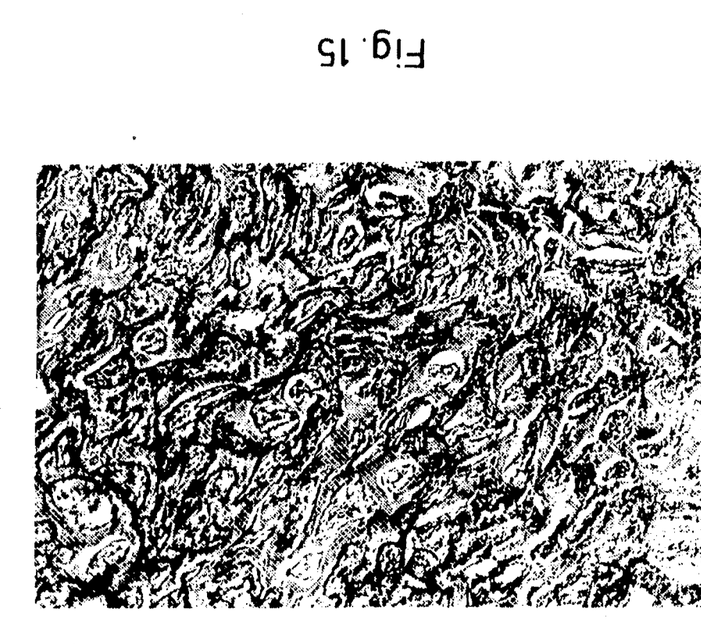
Figure 16:
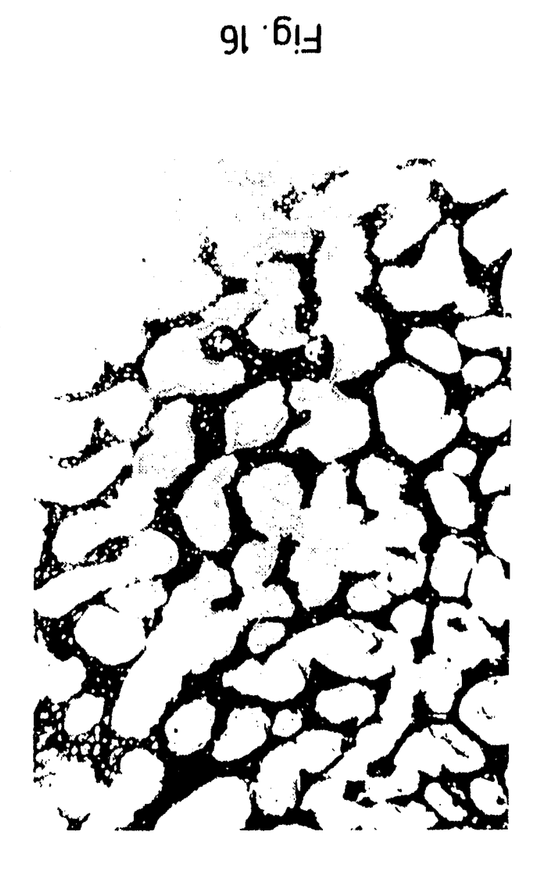
Figure 17:
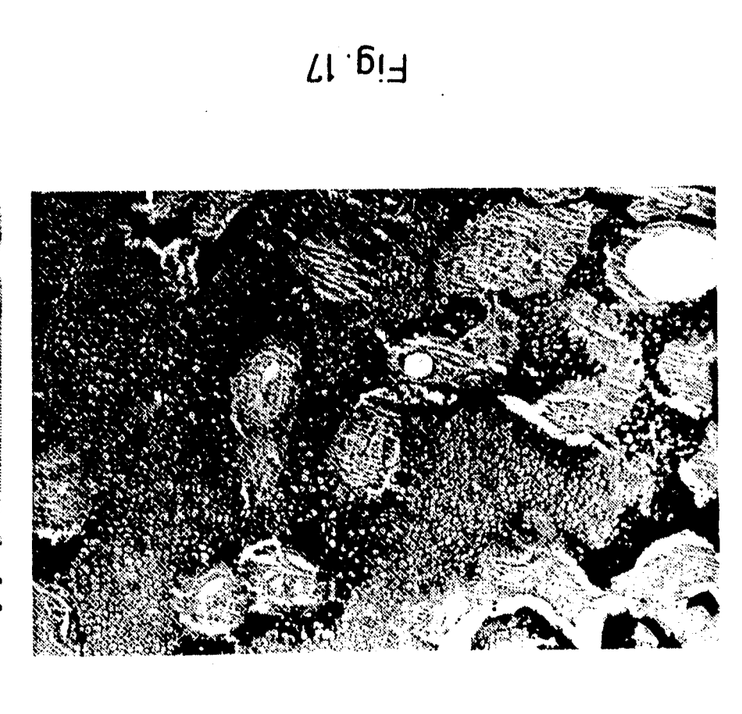
Figure 18:
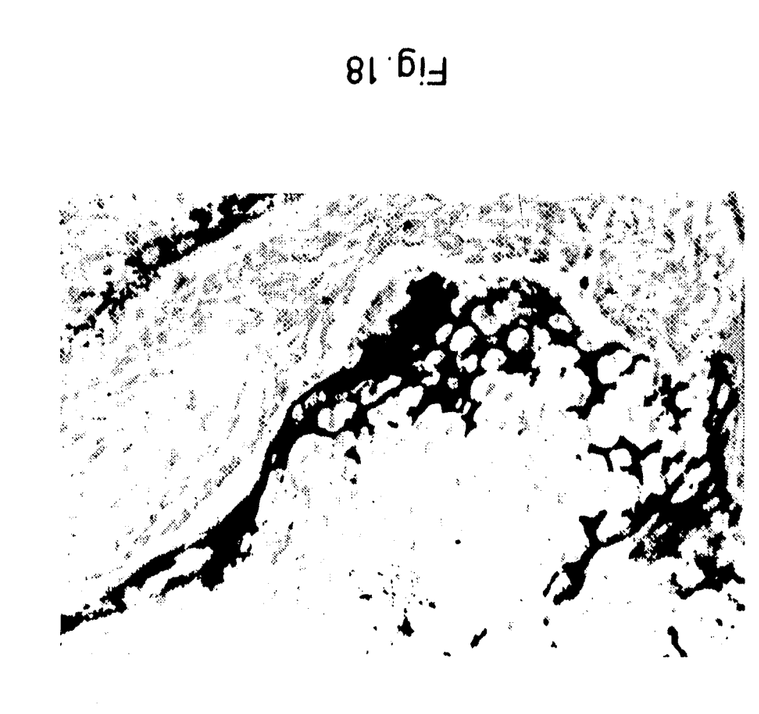

FIGS. 11 to 18 were taken from the 24,25(OH)$_2$D$_3$-treated chicks, 12 days after the fracture, at magnifications $\times$70 (FIGS. 11, 12 and 15 to 17) and $\times$280 (FIGS. 13, 14 and 18). In FIGS. 11 to 14 there can be observed chondrocytes in maturation (hypertrophic in FIG. 13) and many blood vessels in the cartilaginous milieu with osteoid surrounding them (in the centre of FIG. 14). In FIGS. 15 (H&E stain) and 16 (von Kossa stain) new bone formation is seen and in FIGS. 17 and 18 (von Kossa stain)-endochondrial ossification.

A similar set of experiments was carried out with two groups of normal, vitamin D-supplemented chicks, namely a control group and a group treated with the usual 24,25(OH)$_2$D$_3$ in accordance with the above described experimental procedure. The results were similar to those observed in the experiments with the vitamin D-deficient chicks, as described above.

Example 7

The effect of 24,25(OH)$_2$D$_3$ and/or 1,25(OH)$_2$D$_3$ on the mechanical properties of the callus One-day old male chicks were depleted of Vitamin D by feeding them a Vitamin D-deficient diet and by preventing their exposure to ultraviolet light. From day three the birds were treated, every 5 days, by injections of 1.8 $\mu$g of cholecalciferol for the entire experimental period.

Experimental fractures were performed under local anaesthesia with 1% lidocaine. A skin incision was made under sterile conditions, the tibia was exposed and a transverse hole was drilled therethrough with the aid of a dental burr. Light pressure with the fingers caused of transversal fracture of the bone. The chicks were divided into 4 groups. In the first group 50 mg of Bonewax containing 5 $\mu$g of 24,25(OH)$_2$D$_3$ was implanted at the fracture site on both edges of the fractured tibia. In the second group —5 $\mu$g of 1$\alpha$25(OH)$_2$D$_3$ were used, while in the third group a combination of 5 $\mu$g of 1$\alpha$25-(OH)$_2$D$_3$ and 5 $\mu$g of 24,25(OH)$_2$D$_3$ was implanted. The fourth group was implanted with plain bone-wax and served as a control.

Figure 19:
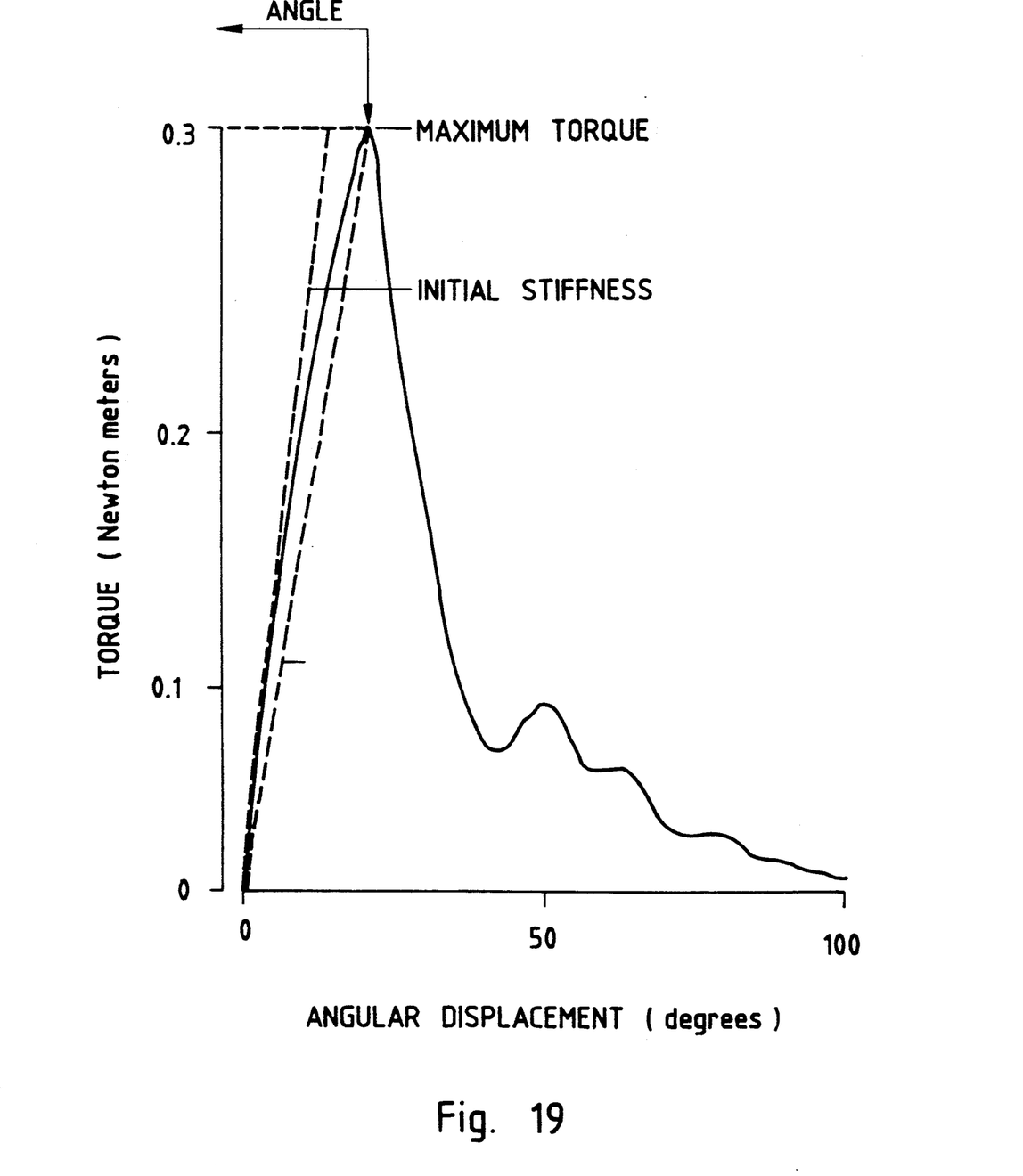
FIG. 19 is a typical torque-angle graph of a callus subjected to a torsional stress, indicating the 4 parameters measured (see Example 7 herein).

The chicks were sacrificed 7 days after the above operation. The fractured tibiae were removed and cleaned. Care was taken not to damage the callus, and the ends were potted in a quick-setting polyester resin. Each bone specimen with its molded ends was subjected to torsional deformation using a Universal Testing Instrument, Model 1126 (Instron, England). The machine was suited for torsion testing and the rate of deformation produced was 180 degrees/min. The strength characteristics of each bone were analysed from the torque-angle graph obtained from each bone specimen. Four parameters were readily measured from each graph (FIG. 19): 1. Maximum torque: 2. Angle; 3. Initial stiffness; and 4. Stiffness.

The mechanical properties of the calluses are represented in the following Table 2 (after 7 days of fracture healing). The "strength" of the callus was lower than the normal unbroken tibia. This is as predicted for a 7 days formation of new bone. 24,25(OH)$_2$D$_3$ increased significantly the "strength" of the callus expressed in maximum torque and the initial stiffness, as compared with the other groups, especially the 1,25(OH)$_2$D$_3$-treated group.

The elastic property of the callus is obtained by the cartilaginous tissue. The increased angle of the 24,25(OH)$_2$D$_3$-treated group is compatible with the morphological changes which occurred in the callus (see Example 6).

A similar set of experiments was carried out, except that the chicks were sacrificed 14 days after the implantation with the bone-wax, i.e. after 14 days of healing. No relevant mechanical data in respect of the callus could, however, be obtained because in three out of the four treated groups it was surprisingly found that, upon testing, the bone broke not at the original fracture site but rather in different places, indicating that the healed fracture site was stronger than the remaining sections of the bone. The exception was the control group, wherein about 50% of the specimens broke at the original fracture site, whereas the remaining 50% broke at other portions of the specimen. The obvious conclusion is that in the three groups treated with the vitamin $D_3$ derivatives the callus was about twice as strong as in the control group.

In the last-mentioned series of experiments it is also relevant to note that only the birds of the control group still showed considerable limping after 14 days of healing.

Conclusion

Calluses formed in response to local implantation of $24,25(OH)_2D_3$ were found to be the strongest ones from a mechanical point of view.

enzyme extracts by the Lowry method, and the results were expressed as units per mg protein.

One unit of phosphatase is defined as the enzyme activity that liberated 1 $\mu$mol of p-nitrophenol per 0.5 h at 37° C.

Results and Discussion

As shown in the following Tables 3 and 4 there is a marked reduction in the AP activity after local administration of $24,25(OH)_2D_3$.

The decreased activity of this enzyme correlates well with our findings (Table 5 below) when we determined AP activity in the epiphyses and diaphyses of normal chicks in comparison with rachitic birds; as well as with the published data in references (3,4). Shedden showed a loss of alkaline phosphatase activity close to a fracture site. This diminution of activity was not caused by the death of the cells in this region, close to the fracture, because a similar result was found in the periosteal cells in subperiosteal fractures (in which the periosteum was intact).

Conclusion

Local treatment with $24,25(OH)_2D_3$, either by direct injection to the epiphyseal growth plate or by implantation into the fracture site reduces alkaline phosphatase activity which is indicative of a better healing process.

TABLE 2

| | | Mechanical properties of the callus* | | |
|---|---|---|---|---|
| Group | n | Meximal Torque (N.m) × $10^{-2}$ | Angle (degrees) | Initial Stiffness (N.m/deg. × $10^3$) | Stiffness (N.m/deg. × $10^3$) |
| Normal ƒ | 7 | 28.71 ± 1.81** | 33.3 ± 2.6 | 10.25 ± 0.82 | 8.84 ± 0.71 |
| Control 4 | 4 | 15.88 ± 1.68 | 56.0 ± 6.9 | 3.65 ± 0.40 | 3.01 ± 0.56 |
| $1,25(OH)_2D_3$ | 6 | 13.89 ± 1.83 | 62.5 ± 5.3 | 3.24 ± 0.38 | 2.24 ± 0.24 |
| $24,25(OH)_2D_3$ | 5 | 20.53 ± 2.05 | 81.4 ± 5.5 | 4.10 ± 0.37 | 2.53 ± 0.27 |
| $1,25(OH)_2D_3$ + $24,25(OH)_2D_3$ | 6 | 15.27 ± 1.15 | 79.8 ± 10.4 | 2.67 ± 0.36 | 2.10 ± 0.34 |

*Determined after 7 days of healing
**MEAN-SEM
ƒNORMAL - unbroken tibia

Example 8

The effect of intra epiphyseal injection and local implantation of $24,25(OH)_2D_3$ on alkaline phosphatase activity Introduction Alkaline phosphatase activity serves as a biochemical parameter for bone formation (1), but its exact role is still unclear (2). In order to quantitate the changes in endochondral ossification which occur in the epiphyseal growth plate and in the callus after local administration of $24,25(OH)_2D_3$, we measured the alkaline phosphatase activity (AP).

Design of the experiments

1. See Example 5 herein for the intraepiphyseal model of injection of $24,25(OH)_2D_3$.
2. See Example 6 herein for experimental callus formed in normal and $-D$ chicks.

After 10 days (3 injections with 3 days intervals) in the intraepiphyseal injection model; and 7 days in the callus forming model, the chicks were killed. The epiphyseal growth plates and the calluses were dissected, weighed and homogenized with the aid of a Polytron homogenizer in ice-cold 0.15M NaCl containing 3 mM of $NaHCO_3$ (pH 7.4), and centrifuged at 20,000 × g for 15 min. at 4° C. The supernatants were assayed for alkaline phosphotase in 0.1M Sodium Barbital buffer, pH 9.3 with p-nitrophenyl phosphate (purchased from "Sigma") as a substrate. Protein was determined in the

TABLE 3

The effect of AP activity in calluses treated locally with $24,25(OH)_2D_3$

| Group | Alkalinephosphatase activity U/mg protein |
|---|---|
| +D - control | 5.3 ± 0.5* |
| +D; $24,25(OH)_2D_3$-treated | 4.1 ± 0.4 |
| −D - control | 4.2 ± 0.7 |
| −D; $24,25(OH)_2D_3$-treated | 2.9 ± 0.4 |

*mean of 5 measurements ± SEM

TABLE 4

The influence of direct injection of $24,25(OH)_2D_3$ into the epiphyseal growth plate on AP activity in rachitic chicks.

| | Alkaline phosphatase activity | |
|---|---|---|
| Group | U/mg tissue | U/mg protein |
| ƒ control | 109.5 ± 34.8* | 14.8 ± 4.0 |
| $24,25(OH)_2D_3$-treated | 48.3 ± 13.0 | 10.5 ± 2.4 |

*mean of 5 measurements ± SEM
ƒ the control is the contralateral epiphyses to the injected ones

TABLE 5

Comparison of AP activity in the epiphyses and diaphyses obtained from normal (+D) and rachitic (−D) chicks

| Group | AP activity U/mg protein |
|---|---|
| +D epiphysis | 3.9 ± 0.7* |
| −D epiphysis | 9.6 ± 2.0 |
| +D diaphysis | 2.6 ± 0.4 |
| −D diaphysis | 16.0 ± 1.8 |

*Mean of 5 measurements ± SEM

REFERENCES

1. Salomon C. D., 1974, A fine structural study on the extracellular activity of alkaline phosphatase and its role in calcification. Calcif. Tiss. Res. 15:201-204
2. Kahn, S. E., Jafri, A. M., Lewis, H. J., Arsenis, C., 1978, purification of alkaline phosphatase from extracellular vesicles of fracture callus cartilage. Calcif. Tiss. Res. 25:85-92
3. Engstrom, C., Granstrom, G., 1982. Alkaline phosphatases in endochondral ossification of rats low in calcium and vitamin D deficient. Acta Orthop Scand. 53:317-323
4. Shedden, R., Dunham, J., Bitensky, L., Catterall, A., Chayen, J., 1976.Changes in alkaline phosphatase activity in periosteal cells in healing fractures. Calcif. Tiss. Res. 22:19-25

What is claimed:

1. A composition for the treatment and promotion of healing of bone fracture and osteotomies in warm-blooded animals including humans by bringing the composition into direct contact with the bone fracture or osteotomy by local application thereof, said composition comprising
   as carrier an orthopedic implant or prosthesis having incorporated therein or thereon from 0.002 to 0.2% by weight of 24,25(OH)$_2$D$_3$ in combination with a physiologically compatible vehicle suitable for use in orthopedic surgery.

2. A composition according to claim 1 which comprises from 0.005 to 0.05% by weight of 24,25(OH)$_2$D$_3$.

3. A composition according to claim 1 wherein said carrier is selected from the group consisting of bonewaxes, bone cements, bone sealants, and demineralized bone powder.

4. A composition according to claim 1 wherein said implant is selected from the group consisting of gelfoam, dacron mesh, and kiel bone.

5. A composition according to claim 1 further comprising one or more auxiliary substances selected from the group consisting of 1α(OH)D$_3$, 1,25(OH)$_2$D$_3$, estradiol, hydroxyapatite crystals, fluoroapatite crystals and growth-hormone.

6. The composition of claim 1, wherein said vehicle is an oil.

7. The composition of claim 6, wherein said vehicle is arachis oil.

8. A composition according to claim 1 further comprising 1,25(OH)$_2$D$_3$ as an auxiliary substance.

9. A method for the treatment and promotion of healing of bone fractures and osteotomies in warm-blooded animals including humans, which comprises
   bringing a therapeutically effective amount of 24,25(OH)$_2$D$_3$ into direct topical contact with the bone fracture or osteotomy by local application directly to and at the site of the fracture or osteotomy of said therapeutically effective amount of 24,25(OH)$_2$D$_3$ dissolved or dispersed in a suitable physiologically compatible carrier.

10. A method according to claim 9 wherein a solution of 24,25(OH)$_2$D$_3$ in a suitable solvent is injected onto the cartilage growth plate of the bone to be treated.

11. A method according to claim 10 wherein said solvent is an oil.

12. A method according to claim 11 wherein said solvent is arachis oil.

13. A method according to claim 9 wherein the 24,25(OH)$_2$D$_3$ dissolved or dispersed in the carrier is locally applied during open surgery to the site of the bone fracture or osteotomy.

14. A method according to claim 13 wherein said carrier is selected from the group consisting of bonewaxes, bone cements, bone sealants, and demineralized bone powder.

15. A method according to claim 13 wherein the 24,25(OH)$_2$D$_3$ is incorporated in a conventional orthopedic implant.

16. A method according to claim 15 wherein said implant is selected from the group consisting of gelfoam, dacron mesh, and kiel bone.

17. A method according to claim 15 wherein the 24,25(OH)$_2$D$_3$ is applied onto the surface of an orthopedic prosthesis.

18. A method according to claim 9 wherein the 24,25(OH)$_2$D$_3$ is locally applied in combination with one or more auxiliary substances selected from the group consisting of 1α(OH)D$_3$, 1,25(OH)$_2$D$_3$, estradiol, hydroxyapatite crystals, fluoroapatite crystals and growth hormone.

19. A method according to claim 9 wherein the 24,25(OH)$_2$D$_3$ is locally applied in combination with 1,25(OH)$_2$D$_3$.

* * * * *